United States Patent
Carchidi et al.

(10) Patent No.: US 6,887,275 B2
(45) Date of Patent: May 3, 2005

(54) MAXILLOFACIAL ANCHORING SYSTEM FOR ALVEOLAR AND SMALL BONE SKELETAL DISTRACTION

(75) Inventors: Joseph Edward Carchidi, West Bridgewater, MA (US); Alan R. Balfour, Petaluma, CA (US)

(73) Assignee: ACE Surgical Supply Co., Inc., Brockton, MA (US)

( * ) Notice: Subject to any disclaimer, the term of this patent is extended or adjusted under 35 U.S.C. 154(b) by 410 days.

(21) Appl. No.: 10/017,219

(22) Filed: Dec. 15, 2001

(65) Prior Publication Data

US 2003/0114857 A1 Jun. 19, 2003

(51) Int. Cl.[7] ................................................. A61F 2/44
(52) U.S. Cl. ...................................................... 623/17.17
(58) Field of Search .............................. 606/69–73, 87; 623/17.17–17.18; 433/173–176

(56) References Cited

U.S. PATENT DOCUMENTS

| | | | |
|---|---|---|---|
| 4,365,958 A | | 12/1982 | Vlock |
| 4,439,152 A | * | 3/1984 | Small ........................ 433/173 |
| 5,709,686 A | * | 1/1998 | Talos et al. ................... 606/69 |
| 5,769,637 A | * | 6/1998 | Morgan ...................... 433/176 |
| 5,769,898 A | * | 6/1998 | Jisander ...................... 424/423 |
| 5,899,696 A | * | 5/1999 | Shimoda ..................... 433/173 |
| 5,899,940 A | | 5/1999 | Carchidi et al. |
| 6,325,803 B1 | * | 12/2001 | Schumacher et al. ......... 606/71 |
| 2001/0012607 A1 | * | 8/2001 | Robinson ................... 433/215 |
| 2002/0062127 A1 | * | 5/2002 | Schumacher et al. ......... 606/70 |

* cited by examiner

Primary Examiner—Glenn K. Dawson
Assistant Examiner—D. Jacob Davis
(74) Attorney, Agent, or Firm—John A. Haug

(57) ABSTRACT

A maxillofacial anchoring and distraction system having an internally threaded anchoring or distraction fixture (12) and a selected length jack screw (14) for placement in an osteotomy. To minimize required bone height, a cut-away bone screw (16) or a solid mesh tip (17) is provided for insertion in bone in a direction generally perpendicular to the longitudinal axes of the anchoring and jack screws. A flat surface portion (16c, 17a) serves as a reaction surface for the distal end of the jack screw. In a second embodiment a sealing screw (24) is used with distraction fixture (20) modified to include a sealing surface. After completion of distraction the sealing screw is used to seal off the distraction fixture for conversion into an implant suitable for receiving conventional prosthetic components.

6 Claims, 4 Drawing Sheets

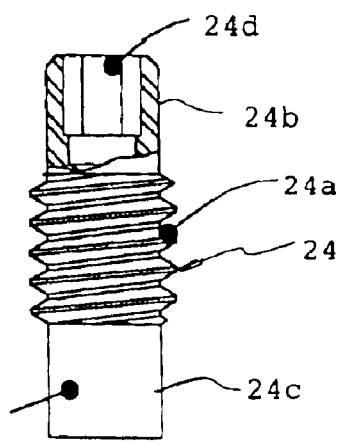
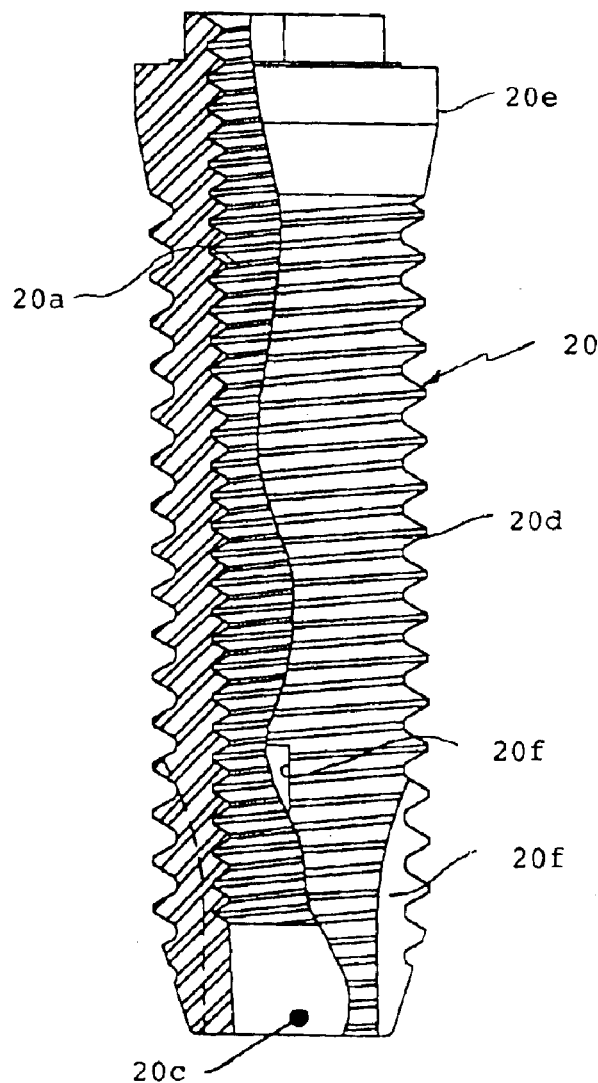
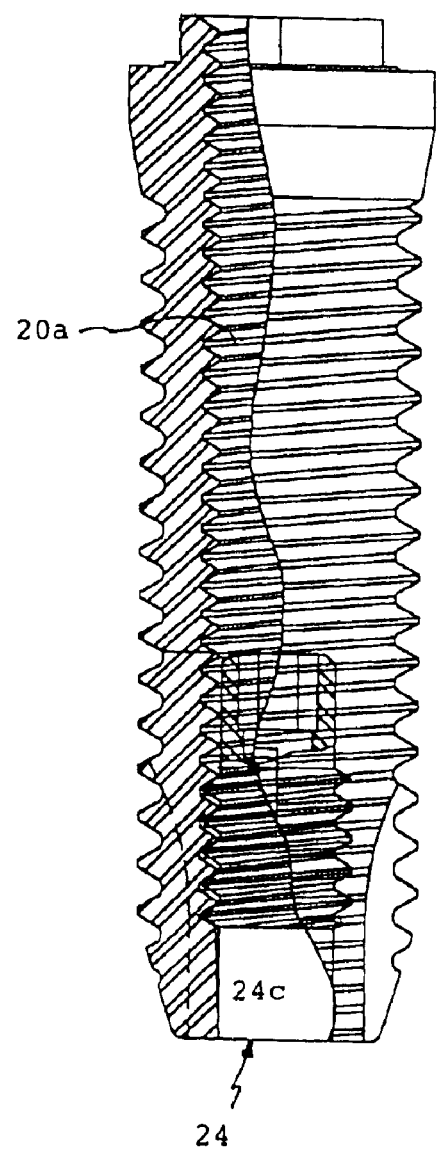
FIG. 4  FIG. 5

MAXILLOFACIAL ANCHORING SYSTEM FOR ALVEOLAR AND SMALL BONE SKELETAL DISTRACTION

FIELD OF THE INVENTION

This invention relates generally to anchoring and fixation systems for bone lengthening by monofocal distraction osteogenesis and more particularly to maxillofacial alveolar and small craniofacial skeletal distraction.

BACKGROUND OF THE INVENTION

The present invention addresses problems associated with regenerating maxillofacial bone mass to treat congenital or functional masticatory deficiencies. Conventionally, in order to overcome masticatory deficiencies, a patient with marginal bone mass is first treated with a surgical bone graft. Bone grafting techniques range from a harvested autogenous onlay graft to a synthetic hydroxyapatite bone mixture used to pack and build up a surgical site. Once the graft has healed, a second surgery is performed to insert the appropriate length endosseous dental implant and to provide masticatory function.

The process of bone grafting to regenerate bone mass has suffered from limited results. In many cases, at the time for surgical insertion of the endosseous dental implant, the grafting mass has significantly or completely resorbed away. One reason for the loss of this grafting material is the body's requirement for an applied stress to stimulate and maintain bone mass. Furthermore, as documented cases have shown, it is not uncommon for the filler material to migrate from the surgical site. This migration and degradation of the graft material minimizes the benefit of the procedure. These undesired results combined with the morbidity of the harvested area demonstrate the need for an alternative surgical procedure. In addition, these conventional multiple surgical procedures require a greater investment of time, money and available grafting materials than is desirable.

In U.S. Pat. No. 5,889,940, assigned to the assignee of the present invention, the subject matter of which is incorporated herein by this reference, a maxillofacial anchoring and distraction system for bone lengthening and distracting osteogenesis is disclosed and claimed comprising an internally threaded base plug for placement in a corticotomy that acts as a base plate for resisting and translating the distraction force, an internally and externally threaded anchoring screw body for locking into the coronal portion of the corticotomy and a defined length distraction jack screw for applying the distraction force. Upon preparation of an osteotomy, the base plug and anchoring screw body are placed therein and the distraction jack screw is inserted. The distraction screw is advanced a selected amount on a periodic basis applying a distraction force on the base plug. When the desired amount of distraction has been achieved, the jack screw is removed and replaced with a healing screw. After a suitable healing period, the healing screw is removed followed by the anchoring screw body and the base plug. A suitable endosseous dental implant is then inserted in a conventional manner. Although the above described apparatus and procedures are very effective, there is a need or desire to provide enhancements in certain case situations. In one such case, the situation relates to the lack of sufficient bone height and/or stability to accommodate the components described in the above referenced patent. In another such case, there is adequate bone height but distraction is necessary to translate the coronal aspect of the implant to its required axial location.

SUMMARY OF THE INVENTION

It is an object of the present invention to provide a system which answers the above noted needs and desires. Another object of the invention is the provision of an apparatus for distracting and increasing the bone mass of the alveolar and small craniofacial skeletal bones by monofocal distraction when minimal bone height and/or stability is available. Yet another object of the invention is to provide an apparatus for converting a coronal distraction fixture, such as that described in U.S. Pat. No. 5,899,940, into a standard implant once distraction is complete.

Briefly described, according to a feature of the first embodiment of the invention, a threaded, cut-away bone screw, or in a modified embodiment, a thin mesh element, is used as a low profile base plug for resisting and translating the downward distraction force in cases of minimal bone height. Either the bone screw or the thin mesh element is used with the anchoring distraction fixture and the defined length distraction jack screw set forth in the above noted patent. The cut-away bone screw or a tip portion of the thin mesh element is used in place of the base plug and is installed in a direction generally perpendicular to the longitudinal axis of the anchoring screw body. According to a feature of the second embodiment of the invention, an externally threaded sealing screw is used to seal the base of a modified coronal distraction fixture and convert it into a standard implant. In this embodiment, the distraction fixture is used with the defined length jack screw and base plug set forth in the above noted patent.

Additional objects and features of the invention will be set forth in part in the description which follows and in part will be obvious from the description. The objects and advantages of the invention may be realized and attained by means of the instrumentalies and combinations particularly pointed out in the appended claims.

BRIEF DESCRIPTION OF THE DRAWINGS

The accompanying drawings, which are incorporated in and constitute a part of the specification, illustrate preferred embodiments of the invention and, together with the description, serve to explain the objects, advantages and principles of the invention. In the drawings:

FIG. 4 is a view similar to FIG. 3 but showing the externally threaded anchoring screw body or distraction fixture along with a sealing screw prior to insertion into the fixture, and FIG. 5 is a view similar to FIG. 4 but shown with the sealing screw inserted into the fixture.

DETAILED DESCRIPTION OF THE PREFERRED EMBODIMENTS

Figure 1:
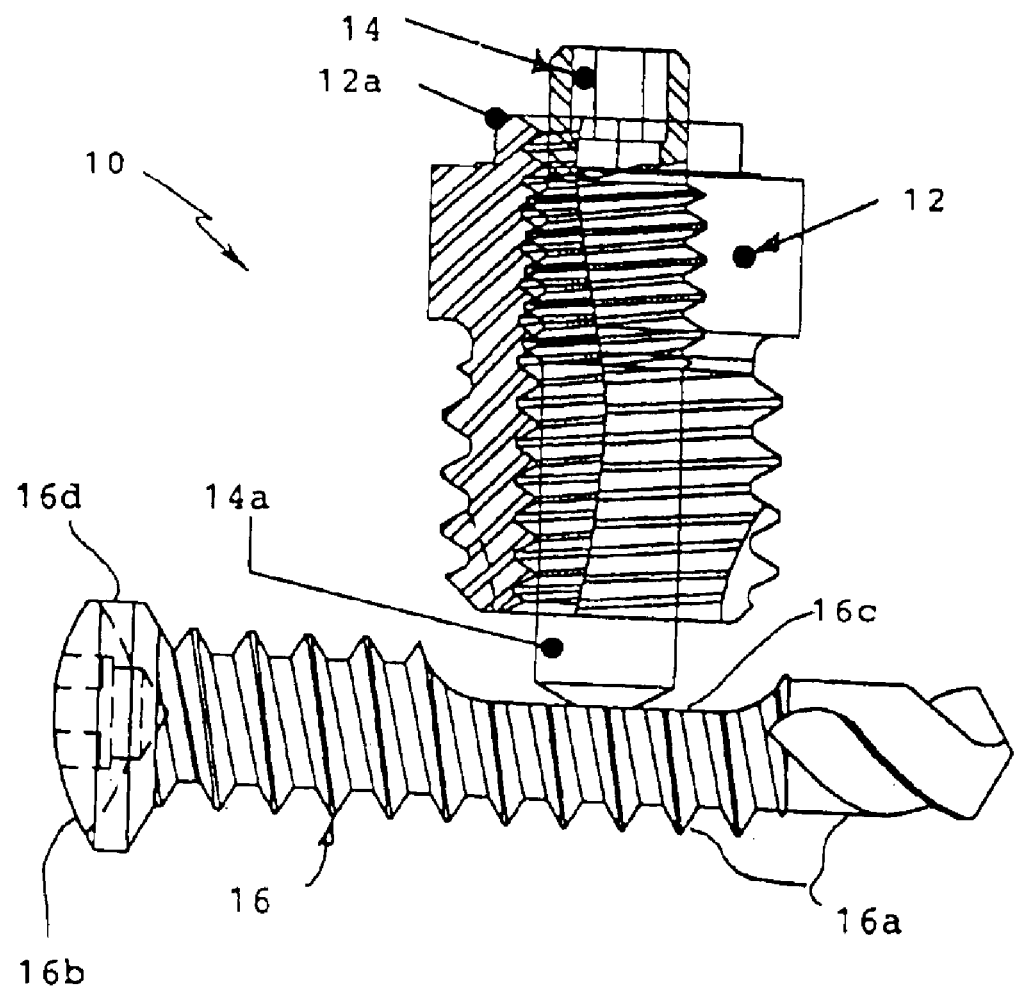
FIG. 1 is a side elevational view, partly in cross section, of a distraction system using a cut-away bone screw as a low profile distraction base plug in accordance with a feature of the first embodiment of the invention.

As shown in FIG. 1, maxillofacial anchoring and distraction system 10 made in accordance with a first preferred embodiment of the invention comprises an externally threaded anchoring screw or distraction fixture 12 and a selected (short, as shown) length jack screw 14 similar to anchoring screw 12 and jack screw 16 disclosed in the above referenced patent, along with a bone screw 16. Bone screw 16 is formed with an external self-tapping bone screw thread 16a and a standard drive bone screw head 16b. A cut-away flat surface portion 16c is formed in the self-tapping screw thread 16a of screw 16, as by machining, preferably in the center of the longitudinal length of the thread, so that when lined up perpendicularly with the alveolar distraction fixture 12, as shown in the drawing, the flat surface portion serves as a reaction surface for jack screw 14 to distract against. To assure appropriate alignment of the cut-away flat surface index portion 16c relative to the distraction fixture 12 and jack screw 14, bone screw 16 is formed, as by milling, with a flat surface index portion 16d formed on the otherwise circular outer periphery of head 16b. Head 16b is referenced, angularly aligned and driven with appropriate mating driver tools (not shown). To further assist in the exact placement of screw 16 relative to distraction fixture 12, an external drilling template that engages a coronal hexagonal portion 12a of distraction fixture 12 can be used. Additionally, as shown in FIG. 1 cut-away flat surface portion 16c extends in length preferably over twice the diameter of distal end 14a of jack screw 14 to allow for thickness variations in patients; cortical bone plates. To further assure the rigid and stable engagement of the bony segment for distraction, bone screw 16 is designed in multiple lengths to accommodate variations in bony plate dimensions. Once distraction and callus healing is complete, the threaded cut-away bone screw can be removed during the removal of distraction fixture 12 or left in place in accordance with the physician's requirements. Thus in cases where there is insufficient bone height or stability to use a normal base plug, the cut-away bone screw serves as the base plug to resist and transfer the downward distraction force from the distraction jack screw. The cut-away bone screw engages the cortical plates of the attached apical bone stock allowing the freed coronal subperiosteal corticotomy segment to distract against the distraction jack screw. Use of the distraction bone screw results in a rigid stabilization of remaining bone stock for distraction as well as in the decrease in the required bone height needed for distraction by up to 3 to 4 millimeters.

Figure 2:
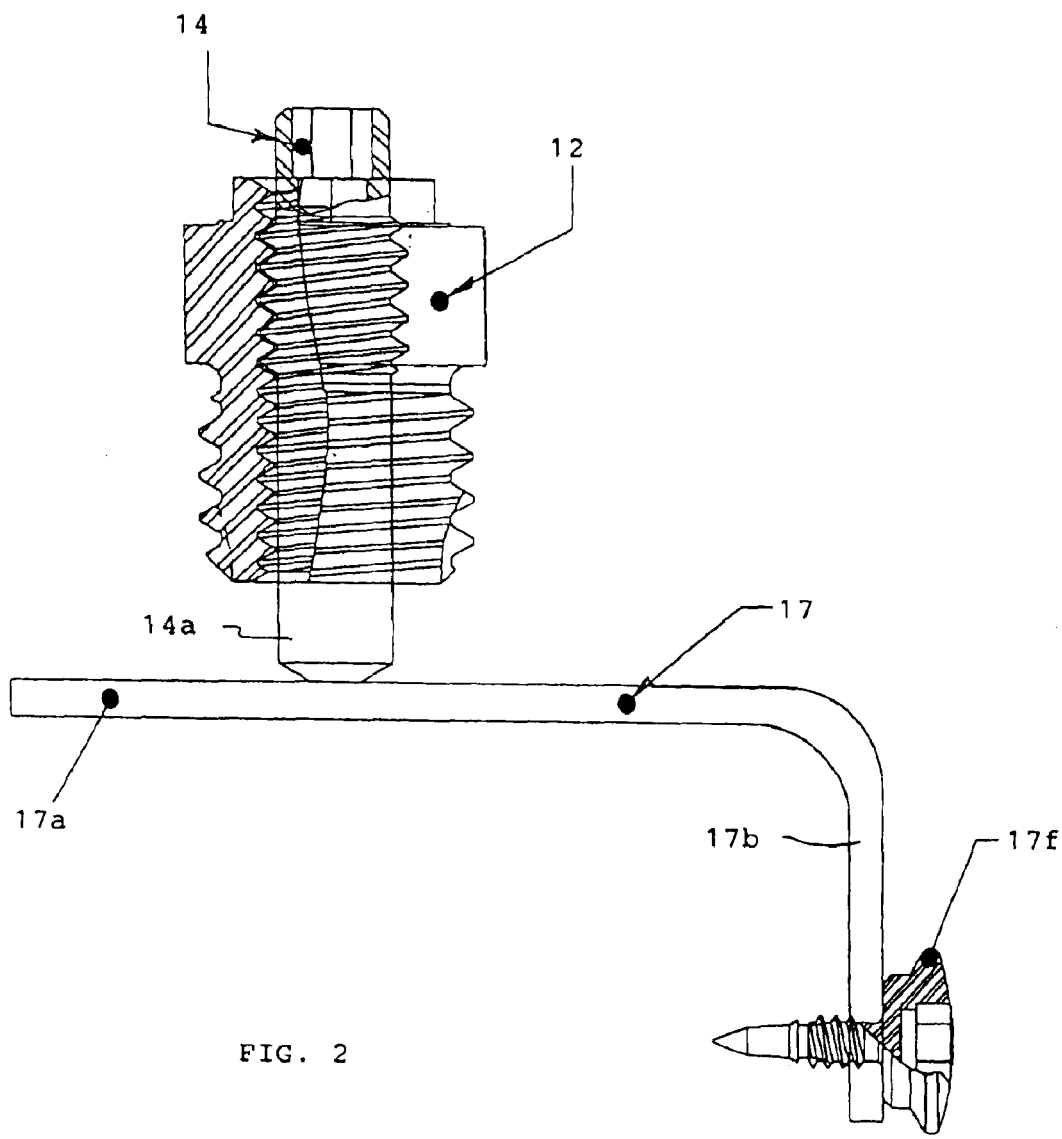
FIG. 2 is a side elevational view of a distraction system using a thin mesh element as a low profile distraction base plug in accordance with a modification of the FIG. 1 embodiment of the invention.
Figure 2A:
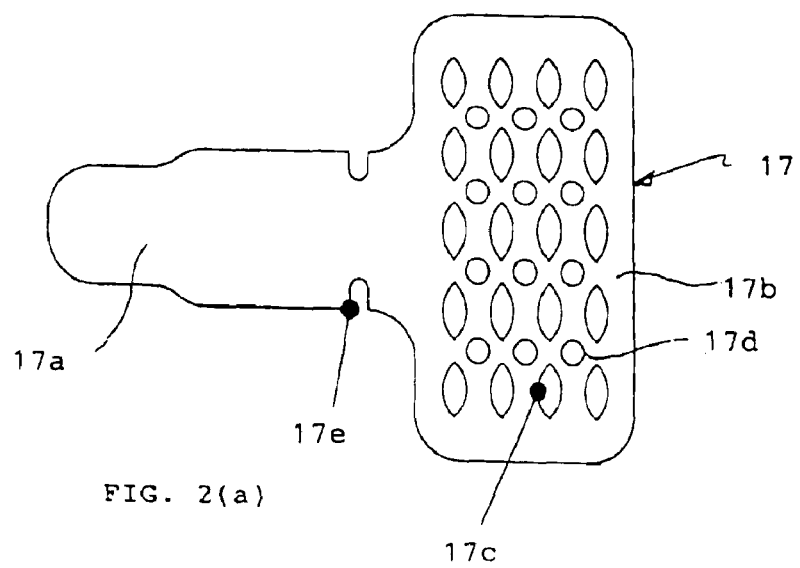
FIG. 2(a) is a top plan view, in reduced scale, of the thin mesh element of the FIG. 2 distraction system, but shown prior to bending into the configuration shown in FIG. 2.

In a modified embodiment, another form of a low profile base plug, as shown in FIGS. 2,2(a), is shown particularly adapted for use when sufficient bone height or stability is unavailable to insert the standard base plug. This low profile base plug or thin base plate mesh element 17 made according to the modified embodiment is composed of suitable material, such as titanium, and comprises a solid, relatively thin tip 17a extending from an integrally attached, relatively wide, modifiable, fixation mesh body 17b. Preferably, a plurality of elongated eye holes 17c and circular pin holes 17d are formed through the fixation mesh body 17b to allow either a fixation bone screw tack 17f or bone screw (not shown) to secure the mesh body to the bony apical segment of a patient. The eye and pin holes also allow for fixation mesh body 17b to be cut down or trimmed as desired to accommodate a selected geometry. In order to use the base plate mesh element 17 to distract against, a surgeon will bend solid mesh tip 17a at grooves 17e and insert the tip through a prepared horizontal osteotomy. Once the mesh tip 17a is inserted through the horizontal osteotomy which is formed perpendicular to the position of the distraction jack screw 14, and laid flat on the apical bony segment, alveolar distraction fixture 12 can be distracted in an axial direction.

When distraction and callus healing is complete, base plate mesh 17 can be removed during the removal of the distraction fixture 12 or left in place as desired.

Figure 3:
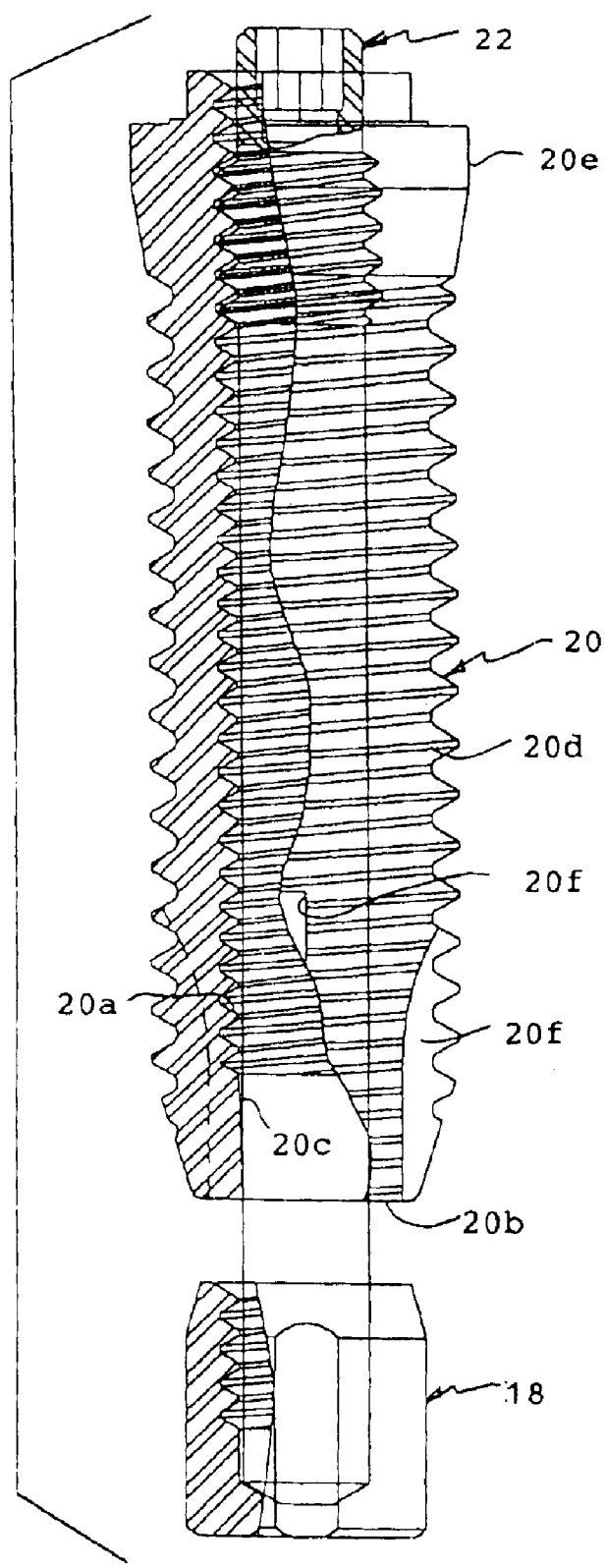
FIG. 3 is a side elevational view of a maxillofacial anchoring and distracting system, partly in cross section, similar to that shown in the above referenced patent, but modified in accordance with the invention.

Turning now to FIGS. 3–5, a second preferred embodiment of the invention will be described. FIG. 3 shows the use of a base plug 18 and jack screw 22 of the type disclosed in the aforementioned patent along with an anchoring screw body or distraction fixture 20 similar to anchor screw body 12 of the patent but modified in accordance with the invention. Fixture 20, typically longer than that shown in the aforementioned patent, is formed with a longitudinally extending bore having a screw thread 20a which extends along its longitudinal length to a selected point inboard of its distal end 20b, forming a distal end sealing portion 20c. Sealing portion 20c is preferably formed as a cylindrical surface having a slight taper of decreasing diameter as one goes in the direction toward the distal end 20b. An external thread 20d, extending from head 20e is preferably formed with cutting flute portions 20f at the distal end portion of fixture 20 which extend generally in a direction parallel to the longitudinal axis of fixture 20. With reference to FIG. 4, sealing screw 24 is formed with an external thread 24a which extends between head or coronal portion 24b and sealing section 24c formed at the distal end portion of screw 24. Sealing surface section 24c preferably is formed as a cylindrical section machined with a unique diametrical size that will frictionally lock and seal off the tapered distal end 20c of distraction fixture 20. By sealing off the distal end 20c of distraction fixture 20, the distraction fixture is converted into a standard implant as shown in FIG. 5. Distraction fixture sealing screw 24 is driven in with a standard female hexagonal driving surface 24d at the head 24b of the screw. Additionally, external threads 24a at the center of the screw are formed so that they exactly match and mate with the distraction fixture 20. The entire length of sealing screw 24, once inserted, allows for the distraction fixture 20, that is converted into a dental implant, to be restored with standard prosthetic components. This embodiment is adapted for use in cases where bone height is available for insertion of a standard length implant but distraction is necessary to transport the coronal aspect of the implant to its required axial location. Once distraction is completed, no additional surgery is required since the alveolar distraction fixture 20 becomes the standard implant. Base plug 18 is merely left in place and the distraction fixture sealed to form the implant. Additionally, cutting flutes 20f serve to prevent rotation of the fixture/implant as it becomes osseointegrated.

Although the invention has been described with regard to certain preferred embodiments thereof, variations and modifications will become apparent to those skilled in the art. It is, therefore, the intention that the appended claims be interpreted as broadly as possible in view of the prior art to include all such variations and modifications.

What is claimed is:

1. A maxillofacial anchoring and distraction system comprising an anchoring screw body having upper and lower sides and having a longitudinal axis and having a longitudinally extending threaded bore extending through the anchoring screw body from the upper side to the lower side, the anchoring screw body having an external bone screw thread, an elongated generally cylindrical member having head and distal ends and a longitudinal axis, an externally threaded portion for threaded engagement in the threaded bore of the anchoring screw body, the generally cylindrical member being capable of being inserted in the bore of the anchoring screw body with the distal end inserted from the upper side and so that the distal end can extend out of the threaded bore beyond the lower side of the anchoring screw body with the generally cylindrical member being removable through the upper side upon completion of distraction, the head end including a driving surface, and the distal end having a distraction force transferring surface, and a reaction element having a flat surface portion for engagement with the distraction force transferring surface of the distal end of the generally cylindrical member when the cylindrical member is in threaded engagement with the anchoring screw body, the flat surface portion serving as an engagement surface to distract against when the reaction element is placed in a horizontally extending osteotomy in a bone with the flat surface portion of the reaction element generally perpendicular relative to the longitudinal axis of the anchoring screw body and the elongated generally cylindrical member, the reaction element comprising a relatively wide mesh body having a plurality of holes formed therethrough and a narrow, relative to the mesh body, solid tip portion extending from the body, the tip portion provided with the flat surface portion.

2. A maxillofacial anchoring and distraction system according to claim 1 in which the holes comprise both generally circular holes and elongated holes.

3. A maxillofacial anchoring and distraction system according to claim 1 in which a weakened portion is formed between the tip portion and the body.

4. A maxillofacial anchoring and distraction system according to claim 3 in which the weakened portion is formed by opposing slots formed between the tip portion and the body.

5. A maxillofacial anchoring and distraction system according to claim 1 in which the flat surface portion extends approximatelly twice the diameter of the distal end of the elongated generally cylindrical member.

6. A maxillofacial anchoring and distraction system comprising an anchoring screw body having an upper side and a lower side and having a longitudinal axis and having a longitudinally extending threaded bore extending through the anchoring screw body from the upper side to the lower side, the anchoring screw body having an external bone screw thread, an elongated generally cylindrical member having head and distal ends and a longitudinal axis, an externally threaded portion for threaded engagement in the threaded bore of the anchoring screw body, the generally cylindrical member being capable of being inserted in the bore of the anchoring screw body with the distal end inserted from the upper side and the distal end configured so that it can extend out of the threaded bore beyond the lower side of the anchoring screw body and formed with a distraction force transferring surface, the head end including a driving surface, and the distal end having a selected diameter, and a reaction element having a mesh fixation base plate having a plurality of holes formed therethrough and formed with a solid flat surface portion for engagement with the distraction force transferring surface of the distal end of the generally cylindrical member when the cylindrical member is in threaded engagement with the anchoring screw body, the flat surface portion extending along a selected axis a distance greater than the diameter of the distal end of the elongated generally cylindrical member to facilitate lateral alignment of the flat surface portion with the end surface of the distal end, the flat surface portion to serve as an engagement surface to distract against when the flat surface portion of the reaction element is placed in a horizontally extending osteotomy in a bone with the flat surface portion of the reaction element generally perpendicular relative to the longitudinal axis of the anchoring screw body and the elongated cylindrical member.

* * * * *